United States Patent
Spironello

(10) Patent No.: US 10,398,629 B1
(45) Date of Patent: Sep. 3, 2019

(54) DISPOSABLE CLIP/CLAMP FOR USE IN SECURING AN OROGASTRIC FEEDING TUBE TO AN ENDOTRACHEAL TUBE AND METHODS OF MAKING AND USING SAME

(71) Applicant: Steven Joseph Spironello, Easton, PA (US)

(72) Inventor: Steven Joseph Spironello, Easton, PA (US)

(*) Notice: Subject to any disclaimer, the term of this patent is extended or adjusted under 35 U.S.C. 154(b) by 0 days.

(21) Appl. No.: 16/228,079

(22) Filed: Dec. 20, 2018

Related U.S. Application Data

(63) Continuation-in-part of application No. 62/751,685, filed on Oct. 28, 2018, which is a continuation of application No. 62/593,675, filed on Dec. 1, 2017.

(51) Int. Cl.
| | |
|---|---|
| *A61J 15/00* | (2006.01) |
| *A61M 16/04* | (2006.01) |
| *A61M 5/14* | (2006.01) |
| *A61M 16/06* | (2006.01) |
| *A61M 25/02* | (2006.01) |

(52) U.S. Cl.
CPC ........ *A61J 15/0053* (2013.01); *A61M 5/1418* (2013.01); *A61M 16/0497* (2013.01); *A61M 16/0688* (2014.02); *A61M 2025/024* (2013.01); *A61M 2025/026* (2013.01); *A61M 2209/088* (2013.01)

(58) Field of Classification Search
CPC ........ A61M 16/0497; A61M 2209/088; A61M 2025/024; A61M 2025/026; A61M 5/1418; A61J 15/0053
See application file for complete search history.

(56) References Cited

U.S. PATENT DOCUMENTS

| | | | |
|---|---|---|---|
| 5,069,206 A | * 12/1991 | Crosbie | A61M 25/02 128/200.26 |
| 5,551,421 A | 9/1996 | Noureldin et al. | |
| 6,298,525 B1 | 10/2001 | Margo | |
| 6,460,540 B1 | 10/2002 | Klepper | |
| 6,461,363 B1 | 10/2002 | Gadberry et al. | |
| RE39,508 E | 3/2007 | Parker | |
| 7,921,847 B2 | 4/2011 | Totz | |
| 8,099,837 B2 | 1/2012 | Santin et al. | |
| 2002/0162555 A1 | 11/2002 | West et al. | |
| 2009/0229615 A1 | 9/2009 | Stenzler et al. | |

* cited by examiner

*Primary Examiner* — Nathan R Price
*Assistant Examiner* — Anh Bui
(74) *Attorney, Agent, or Firm* — James R. McDaniel

(57) ABSTRACT

A stabilization clip for use in securing an orogastric feeding tube to an endotracheal tube, including a base having a first end and a second end, wherein the base includes an orogastric feeding tube holder and an endotracheal tube holder such that the endotracheal tube holder is located adjacent to the orogastric feeding tube holder, a hinge operatively connected to a first end of the base, a flexible arm having a first end and a second end such that the first end of the flexible arm is operatively connected to the hinge, a locking mechanism located on the second end of the base, and an extension located on the second end of the flexible arm, wherein when the extension is located within the locking mechanism, the clip secures the orogastric feeding tube to the endotracheal tube.

12 Claims, 3 Drawing Sheets

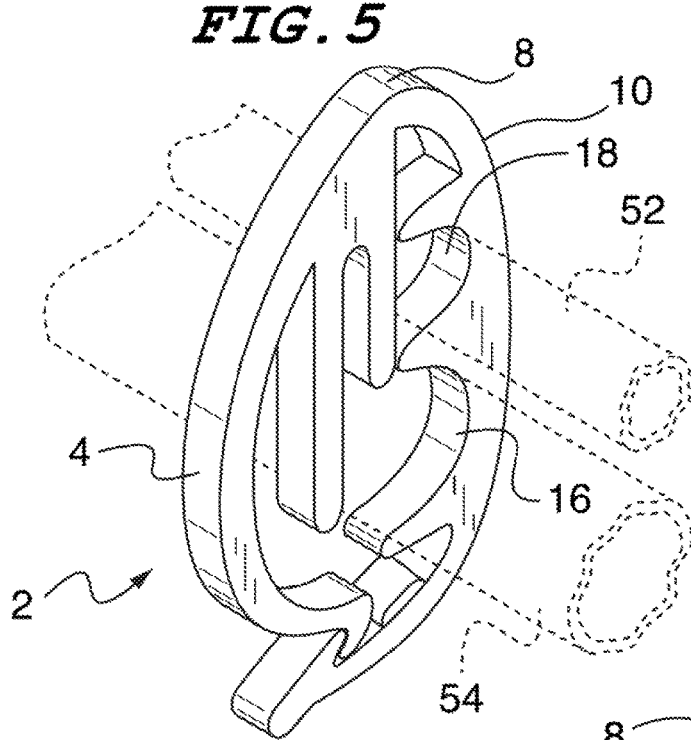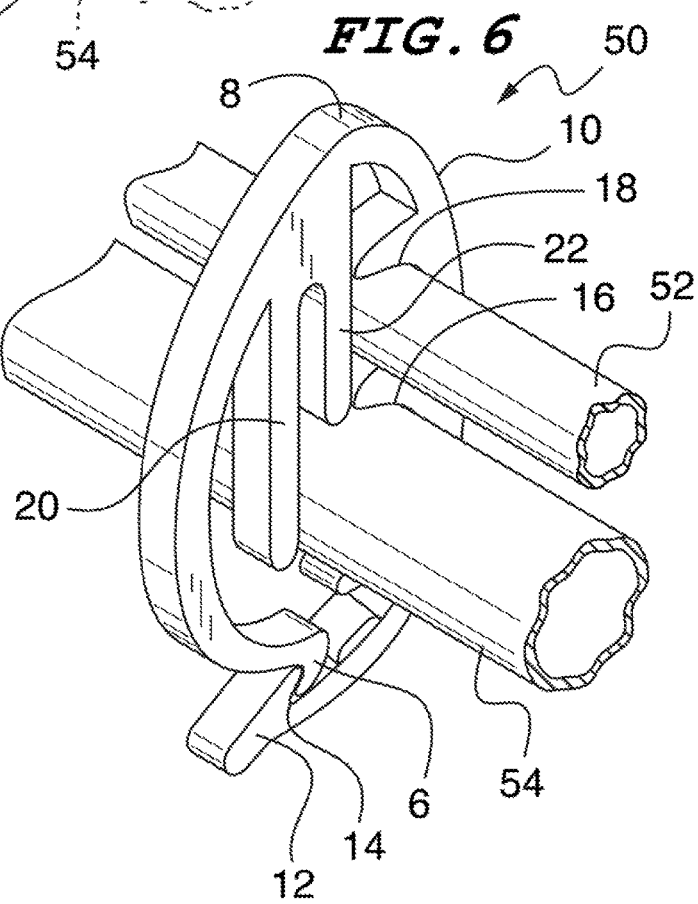

ant al., and U.S. Patent Application 2009/0229615 by Stenzler et al. While these various clips and clamps that are used to attach various surgical tubes to one another may have been generally satisfactory, there is nevertheless a need for a new and improved disposable stabilization clip/clamp device used for the securing of an orogastric feeding tube (OGT) to an endotracheal tube (ETT).

DISPOSABLE CLIP/CLAMP FOR USE IN SECURING AN OROGASTRIC FEEDING TUBE TO AN ENDOTRACHEAL TUBE AND METHODS OF MAKING AND USING SAME

CROSS-REFERENCE TO RELATED APPLICATIONS

This application is a continuation-in-part of U.S. Provisional Patent Application Ser. No. 62/751,685, filed on Oct. 28, 2018, which is a continuation of U.S. Provisional Patent Application Ser. No. 62/593,675, filed on Dec. 1, 2017 the disclosures of which are hereby incorporated by reference in their entirety to provide continuity of disclosure to the extent such disclosures are not inconsistent with the disclosure herein.

FIELD OF THE INVENTION

The present invention is generally related to a disposable stabilization clip/clamp device used for the securing of an orogastric feeding tube (OGT) to an endotracheal tube (ETT). The present invention is designed with the intention to not only properly secure the ETT to the OGT but also to prevent the OGT from dislodging during the intubation phase of patient management.

BACKGROUND OF THE INVENTION

Prior to the present invention, as set forth in general terms above and more specifically below, it is known that in a typical hospital setting, the current practice of securing an orogastric feeding tube (OGT) to an endotracheal tube (ETT) is accomplished by the use of medical grade adhesive tape which is also referred to as surgical tape. The major disadvantage of utilizing surgical tape is that it does not provide a definitive trust worthy method of securing the OGT to the ETT. This is because the surgical tape overtime becomes saturated with humidity and oral secretions, thereby causing the degradation of the adhesive integrity in the surgical tape. Consequently, this allows for the possibility of OGT dislodgement which can cause aspiration of gastric contents as well as tube feedings, if being infused, into the lungs.

Another disadvantage of the surgical tape is that is very difficult to remove once it has been applied around the OGT and the ETT. If the ETT needs to be pulled back or inserted further, the surgical tape makes this process more challenging since it cannot be removed in a quick and safe manner. In fact, there have been instances in which the surgical tape has been so hard to get off that healthcare workers have used scissors to cut the tape and in the process of doing so cut through the ETT.

The final disadvantage of utilizing surgical tape is that the surgical tape may accumulate various types of bacteria overtime making the surgical tape a potential risk factor for the development of ventilator associated pneumonia. Furthermore, the surgical tape does not allow healthcare workers the ability to properly clean the surgical tape nor does the surgical tape allow health care workers to properly clean underneath the ETT.

It is also known, to employ various types of clips and clamps to attach various surgical tubes to one another. See for example, U.S. Pat. No. 5,069,206 by Crosbie, U.S. Pat. No. 5,551,421 by Noureldin et al., U.S. Pat. No. 6,298,525 by Margo, U.S. Pat. No. 6,460,540 by Klepper, U.S. Pat. No. 6,461,363 by Gadberry et al., U.S. Pat. No. 7,921,847 by Totz, U.S. Pat. No. 8,099,837 by Santin et al., RE39,508 by Parker, U.S. Patent Application 2002/0162555 by West et It is a purpose of this invention to fulfill these and other needs in the art of securing an orogastric feeding tube (OGT) to an endotracheal tube (ETT) in a manner more apparent to the skilled artisan once given the following disclosure.

BRIEF SUMMARY OF THE INVENTION

A first aspect of the present invention is a stabilization clip for use in the securing of an orogastric feeding tube to an endotracheal tube, including a base having a first end and a second end, wherein the base includes an orogastric feeding tube holder for holding a portion of an orogastric feeding tube and an endotracheal tube holder for holding a portion of an endotracheal tube such that the endotracheal tube holder is located adjacent to the orogastric feeding tube holder, a hinge operatively connected to a first end of the base, a flexible arm having a first end and a second end such that the first end of the flexible arm is operatively connected to the hinge, a locking mechanism located on the second end of the base; and an extension located on the second end of the flexible arm, wherein when the extension is located within the locking mechanism, the clip secures the orogastric feeding tube to the endotracheal tube.

In one embodiment of the first aspect of the present invention, the clip is a one-piece stabilization clip.

In another embodiment of the first aspect of the present invention, the orogastric feeding tube holder and the endotracheal tube holder are C-shaped.

In a further embodiment of the first aspect of the present invention, the base further includes a release lever located adjacent to the locking mechanism for unlocking the locking mechanism.

In a still another embodiment of the first aspect of the present invention, the flexible arm further includes a flexible orogastric feeding tube tongue located adjacent to the hinge, and a flexible endotracheal tube tongue located adjacent to the orogastric feeding tube tongue, wherein the orogastric feeding tube tongue interacts with the orogastric feeding tube and the endotracheal tube tongue interacts with the endotracheal tube in order to secure the orogastric feeding tube to the endotracheal tube.

In a still further embodiment of the first aspect of the present invention, the endotracheal tube tongue extends over the orogastric feeding tube and the endotracheal tube and the orogastric feeding tube tongue extends over the orogastric feeding tube.

In a yet another embodiment of the first aspect of the present invention, the stabilization clip is constructed of a durable, medical grade, antimicrobial, flexible, disposable material.

A second aspect of the present invention is an orogastric feeding tube and endotracheal tube securing clamp, including a base having a first end and a second end, wherein the base includes an orogastric feeding tube holder for holding a portion of an orogastric feeding tube and an endotracheal tube holder for holding a portion of an endotracheal tube such that the endotracheal tube holder is located adjacent to the orogastric feeding tube holder, a hinge operatively connected to a first end of the base, a flexible arm having a first end and a second end such that the first end of the flexible arm is operatively connected to the hinge, a locking mechanism located on the second end of the base, and an extension located on the second end of the flexible arm, wherein when the extension is located within the locking mechanism, the clip secures the orogastric feeding tube to the endotracheal tube.

In one embodiment of the second aspect of the present invention, the clip is a one-piece stabilization clamp.

In another embodiment of the second aspect of the present invention, the orogastric feeding tube holder and the endotracheal tube holder are C-shaped.

In a further embodiment of the second aspect of the present invention, the base further includes a release lever located adjacent to the locking mechanism for unlocking the locking mechanism.

In a still another embodiment of the second aspect of the present invention, the flexible arm further includes a flexible orogastric feeding tube tongue located adjacent to the hinge, and a flexible endotracheal tube tongue located adjacent to the orogastric feeding tube tongue, wherein the orogastric feeding tube tongue interacts with the orogastric feeding tube and the endotracheal tube tongue interacts with the endotracheal tube in order to secure the orogastric feeding tube to the endotracheal tube.

In a still further embodiment of the second aspect of the present invention, the endotracheal tube tongue extends over the orogastric feeding tube and the endotracheal tube and the orogastric feeding tube tongue extends over the orogastric feeding tube.

In a yet another embodiment of the second aspect of the present invention, the stabilization clamp is constructed of a durable, medical grade, antimicrobial, flexible, disposable material.

A third aspect of the present invention is a method of using a stabilization clip to secure an orogastric feeding tube to an endotracheal tube, including the steps of: providing a base having a first end and a second end, wherein the base includes an orogastric feeding tube holder for holding a portion of an orogastric feeding tube and an endotracheal tube holder for holding a portion of an endotracheal tube such that the endotracheal tube holder is located adjacent to the orogastric feeding tube holder; providing a hinge operatively connected to a first end of the base; providing a flexible arm having a first end and a second end such that the first end of the flexible arm is operatively connected to the hinge; providing a locking mechanism located on the second end of the base; and providing an extension located on the second end of the flexible arm, wherein when the extension is located within the locking mechanism, the clip secures the orogastric feeding tube to the endotracheal tube.

In one embodiment of the third aspect of the present invention, the dip is constructed as a one-piece stabilization clip.

In another embodiment of the third aspect of the present invention, the orogastric feeding tube holder and the endotracheal tube holder are C-shaped.

In a further embodiment of the third aspect of the present invention, the step of providing a base further includes the step of providing a release lever located adjacent to the locking mechanism for unlocking the locking mechanism.

In a still another embodiment of the third aspect of the present invention, the step of providing a flexible arm further includes the steps of providing a flexible orogastric feeding tube tongue located adjacent to the hinge; and providing a flexible endotracheal tube tongue located adjacent to the orogastric feeding tube tongue, wherein the orogastric feeding tube tongue interacts with the orogastric feeding tube and the endotracheal tube tongue interacts with the endotracheal tube in order to secure the orogastric feeding tube to the endotracheal tube.

In a still further embodiment of the third aspect of the present invention, the endotracheal tube tongue extends over the orogastric feeding tube and the endotracheal tube and the orogastric feeding tube tongue extends over the orogastric feeding tube.

The preferred disposable stabilization dip/clamp device for use in the securing of an orogastric feeding tube (OGT) to an endotracheal tube (ETT), according to various embodiments of the present invention, offers the following advantages: ease of use; lightness in weight; durability; disposability; ease of attaching the clip/clamp device to the OGT and ETT; ease of removal of the clip/clamp device from the OGT and ETT; reduced likelihood of the OGT becoming dislodged from the ETT; reduced ability of the dip/clamp to accumulate bacteria; and the ability to be able to clean underneath of the ETT. In fact, in many of the preferred embodiments, these advantages are optimized to an extent that is considerably higher than heretofore achieved in prior, known clip/clamp devices for use in the securing of an orogastric feeding tube (OGT) to an endotracheal tube (ETT).

BRIEF DESCRIPTION OF THE DRAWINGS

The above-mentioned features and steps of the invention and the manner of attaining them will become apparent, and the invention itself will be best understood by reference to the following description of the embodiments of the invention in conjunction with the accompanying drawings, wherein like characters represent like parts throughout the several views and in which:

FIG. 5 is a schematic front view illustration of the disposable stabilization clip/clamp device for use in the securing of an orogastric feeding tube (OGT) to an endotracheal tube (ETT) with the spring arm being shown in a locked position, prior to the orogastric feeding tube (OGT) and the endotracheal tube (ETT) being retained by the stabilization clip/clamp device, according the present invention; and FIG. 6 is a schematic isometric illustration of the disposable stabilization clip/clamp device securing the orogastric feeding tube (OGT) to an endotracheal tube (ETT), according the present invention.

DETAILED DESCRIPTION OF THE PREFERRED EMBODIMENTS OF THE INVENTION

Figure 1:
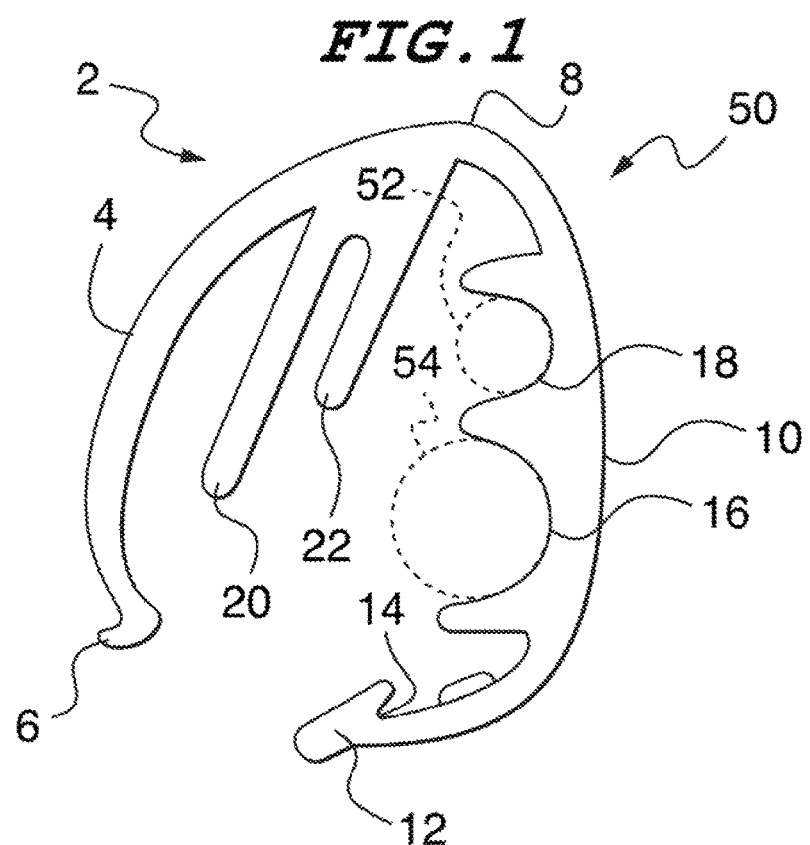
FIG. 1 is a schematic front view illustration of a disposable stabilization clip/clamp device for use in the securing of an orogastric feeding tube (OGT) to an endotracheal tube (ETT), constructed according the present invention.
Figure 2:
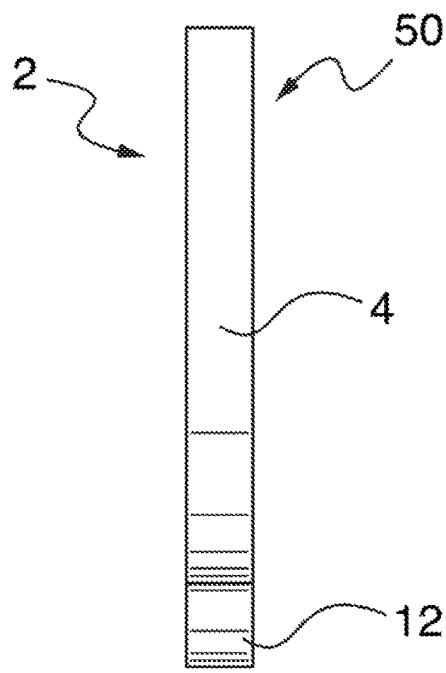
FIG. 2 is a schematic front view of the disposable stabilization dip/clamp device for use in the securing of an orogastric feeding tube (OGT) to an endotracheal tube (ETT), constructed according the present invention.
Figure 3:
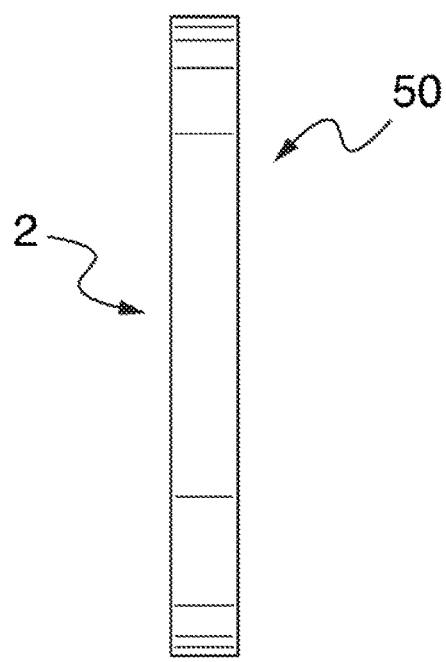
FIG. 3 is a schematic back view of the disposable stabilization clip/clamp device for use in the securing of an orogastric feeding tube (OGT) to an endotracheal tube (ETT), constructed according the present invention.

In order to address the shortcomings of the prior, known devices used for securing an orogastric feeding tube (OGT) to an endotracheal tube (ETT), reference is made now to FIGS. 1-6, where there is illustrated a one-piece, disposable clip/clamp 2 used for the securement of an orogastric feeding tube (OGT) 52 to an endotracheal tube (ETT) 54. As will be explained hereinafter in greater detail, the one-piece, disposable dip/clamp 2 can be used in conjunction with an orogastric feeding tube (OGT) 52 and an endotracheal tube (ETT) 54 in order to releasably secure the orogastric feeding tube (OGT) 52 to an endotracheal tube (ETT) during a medical procedure and/or patient management.

As shown in FIGS. 1-4, there is illustrated a one-piece, disposable clip/clamp 2 that can be used in conjunction with an orogastric feeding tube (OGT) 52 and an endotracheal tube (ETT) 54 in order to releasably secure the orogastric feeding tube (OGT) 52 to an endotracheal tube (ETT) during a medical procedure and/or patient management. One-piece, disposable clip/clamp 2 includes, in part, flexible arm 4, extension 6, hinge 8, base 10, release lever 12, locking mechanism 14, endotracheal tube (ETT) holder 16, orogastric feeding tube (OGT) holder 18, endotracheal tube (ETT) tongue 20, and orogastric feeding tube (OGT) tongue 22. It is to be understood that one-piece, disposable clip/clamp 2, preferably, is constructed of any suitable, durable, medical grade, antimicrobial, flexible, disposable material.

A unique aspect of the present invention is that the disposable clip/clamp 2 is constructed of one-piece and that the disposable clip/clamp 2 is flexible especially the flexible arm, the release lever, the endotracheal tube (ETT) tongue, and the orogastric feeding tube (OGT) tongue. This provides for user-friendly ease in dipping and unclipping of the disposable clip/clamp 2, as will be discussed in greater detail later. It is to be understood that one-piece, disposable clip/clamp 2 may be constructed by conventional material forming techniques such as molding, stamping, forming, casting, thermoforming, or the like.

Another unique aspect of the present invention is the use of extension 6, release lever 12, and locking mechanism 14. As more dearly shown in FIGS. 4-6, extension 6, release lever 12, and locking mechanism 14 can be used in conjunction with each other in order to releasably secure the orogastric feeding tube (OGT) 52 to an endotracheal tube (ETT) 54 during a medical procedure and/or patient management. As will be discussed in greater detail later, once a portion of the orogastric feeding tube (OGT) 52 and the endotracheal tube (ETT) 54 have been located within one-piece, disposable clip/clamp 2, extension 6 can then be located under locking mechanism 14. In this manner, orogastric feeding tube (OGT) 52 is secured to endotracheal tube (ETT) 54. In order to release orogastric feeding tube (OGT) 52 and endotracheal tube (ETT) 54 from one-piece, disposable clip/clamp 2, the end user simply has to press on release lever 12 which should cause extension 6 to become no longer retained by locking mechanism 14 and the flexible arm 4 will pivot away from base 10 by the movement of hinge 8. The movement of the flexible arm 4 away from base 10 should allow the end user to easily remove the orogastric feeding tube (OGT) 52 and the endotracheal tube (ETT) 54 from the one-piece, disposable clip/clamp 2.

Figure 4:
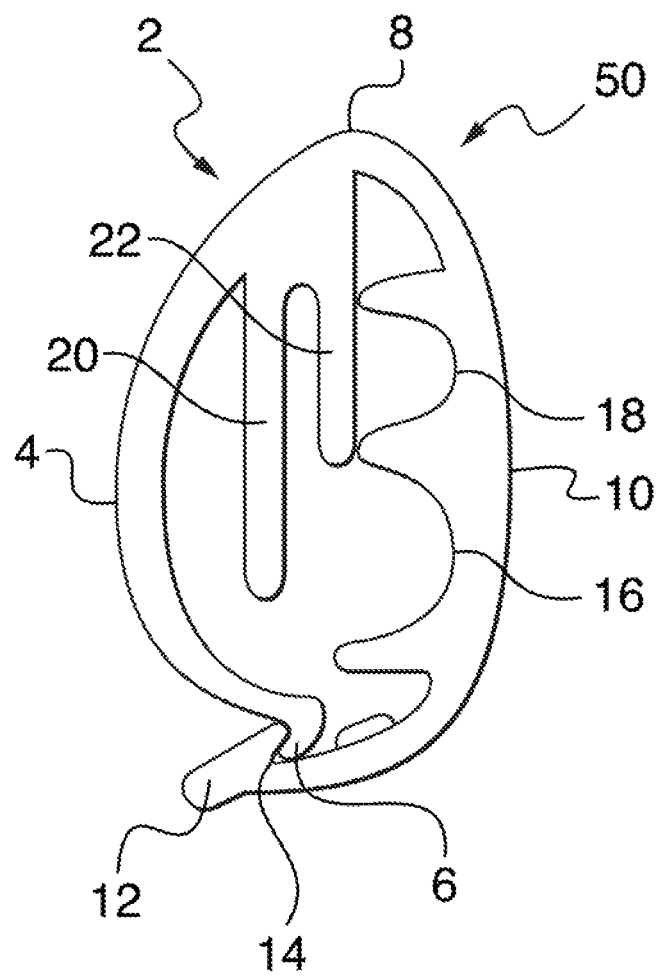
FIG. 4 is a schematic front view illustration of the disposable stabilization dip/clamp device for use in the securing of an orogastric feeding tube (OGT) to an endotracheal tube (ETT) with the spring arm being shown in a locked position, according the present invention.

As shown in FIGS. 1 and 4, located along base 10 are two (2) "C" shaped holders/retainers (endotracheal tube (ETT) holder 16 and orogastric feeding tube (OGT) holder 18). It is to be understood that endotracheal tube (ETT) holder 16 is designed so that it will be able to accommodate various sized endotracheal tubes (ETT) ranging from 6 Fr (French) to 8.5 Fr (French). It is to be understood that the orogastric feeding tube (OGT) holder 18 is designed to accommodate a single sized orogastric feeding tube (OGT) that is consistent with the healthcare industry standard.

A further unique aspect of the present invention is that the one-piece, disposable clip/clamp 2 includes an endotracheal tube (ETT) holder 16 that is designed so that it will be able to accommodate various sized endotracheal tubes. In this manner, the one-piece, disposable clip/clamp 2 can be used in a variety of medical procedures without the need to use a different clip/clamp for different sized endotracheal tubes (ETT). This will cut down on the number of different sizes of clips/clamps that the hospital or surgical facility needs to keep in stock.

Regarding endotracheal tube (ETT) tongue 20 and orogastric feeding tube (OGT) tongue 22, as shown in FIGS. 1 and 4, located within one-piece, disposable clip/clamp 2 are two separate tongues (endotracheal tube (ETT) tongue 20 and orogastric feeding tube (OGT) tongue 22) that protrude over the endotracheal tube (ETT) 54 and the orogastric tube (OGT) 52 to adequately place pressure on the endotracheal tube (ETT) 54 and the orogastric tube (OGT) 52 when the one-piece, disposable dip/clamp 2 is clipped into place, as will be discussed in greater detail later. It is to be understood that endotracheal tube (ETT) tongue 20 should be located above (or away from) orogastric feeding tube (OGT) tongue 22 so that endotracheal tube (ETT) tongue 20 will not interfere with the interaction between orogastric feeding tube (OGT) tongue 22 and orogastric feeding tube (OGT) 52. In particular, endotracheal tube (ETT) tongue 20 will protrude over endotracheal tube (ETT) 54 and the orogastric tube (OGT) 52 and, when clipped into place, should retain endotracheal tube (ETT) 54 within one-piece, disposable clip/clamp 2. Furthermore, orogastric feeding tube (OGT) tongue 22 will protrude only over the orogastric tube (OGT) 52 and, when clipped into place, should retain orogastric tube (OGT) 52 within one-piece, disposable clip/clamp 2 and thereby retaining orogastric feeding tube (OGT) 52 on endotracheal tube (ETT) 54. It is to be understood that endotracheal tube (ETT) tongue 20 and orogastric feeding tube (OGT) tongue 22 should be constructed so that they are rigid enough in order to properly retain the endotracheal tube (ETT) 54 and the orogastric tube (OGT) 52 within the one-piece, disposable clip/clamp 2 (and retain orogastric feeding tube (OGT) 52 on endotracheal tube (ETT) 54) but flexible enough so as to not interfere with (or otherwise create an obstruction in) the flow of materials flowing through the endotracheal tube (ETT) 54 and the orogastric tube (OGT) 52.

Operation of the One-Piece Disposable Clamp

Regarding the operation of one-piece, disposable clip/clamp 2, the end user first determines the size of the endotracheal tube (ETT) 54 to be secured to the orogastric tube (OGT) 52 through the use of one-piece, disposable clip/clamp 2. As shown in FIGS. 1-6, the end user then locates a portion of the orogastric tube (OGT) 52 and a portion of the endotracheal tube (ETT) 54 to be secured by the one-piece, disposable clip/clamp 2 within the one-piece, disposable clip/clamp 2. In particular, the portion of orogastric tube (OGT) 52 is located within orogastric feeding tube (OGT) holder 18 and a portion of endotracheal tube (ETT) 54 is located within endotracheal tube (ETT) holder 16, as discussed earlier After the orogastric tube (OGT) 52 and the endotracheal tube (ETT) 54 have been located within orogastric feeding tube (OGT) holder 18 and endotracheal tube (ETT) holder 16, respectively, the end user simply pushes on flexible arm 4 so that extension 6 becomes retained by locking mechanism 14, as discussed earlier.

Once the extension 6 becomes retained by locking mechanism 14, the endotracheal tube (ETT) tongue 20 and the orogastric feeding tube (OGT) tongue 22 will protrude or otherwise extend over the endotracheal tube (ETT) 54 and the orogastric tube (OGT) 52, respectively to adequately place pressure on the endotracheal tube (ETT) 54 and the orogastric tube (OGT) 52 when the one-piece, disposable clip/clamp 2 is clipped into place. As discussed earlier, endotracheal tube (ETT) tongue 20 will protrude over endotracheal tube (ETT) 54 and the orogastric tube (OGT) 52 and, when clipped into place, should retain endotracheal tube (ETT) 54 within one-piece, disposable clip/clamp 2. Furthermore, orogastric feeding tube (OGT) tongue 22 will protrude only over the orogastric tube (OGT) 52 and, when clipped into place, should retain orogastric tube (OGT) 52 within one-piece, disposable clip/clamp 2. In this manner, orogastric feeding tube (OGT) 52 is secured to endotracheal tube (ETT) 54.

In order to remove the endotracheal tube (ETT) 54 and the orogastric tube (OGT) 52 from one-piece, disposable clip/clamp 2, as discussed earlier, the end user simply has to press on release lever 12 which should cause extension 6 to become no longer retained by locking mechanism 14 and the flexible arm 4 will pivot away from base 10 by the movement of hinge 8. The movement of the flexible arm 4 away from base 10 should allow the end user to easily remove the orogastric feeding tube (OGT) 52 and the endotracheal tube (ETT) 54 from the by the one-piece, disposable dip/clamp 2. In this manner, orogastric feeding tube (OGT) 52 is now not secured to endotracheal tube (ETT) 54.

Another unique aspect of the present invention is that the one-piece, disposable clip/clamp 2 provides a safer and more secure method of "securing" a nasogastric or orogastric feeding tube to the endotracheal tube (ETT) 54 for mechanically ventilated patients, thereby preventing the risk of aspiration.

A still another unique aspect of the present invention is that the one-piece, disposable clip/clamp 2 will provide an enhanced ability to provide improved routine disinfectant care to the endotracheal tube (ETT) 54, while limiting the accumulation of harmful microbials as well as oral secretions. Furthermore, the one-piece, disposable clip/clamp 2 will be cost-effective enough that it can be changed on a daily basis during routine hygiene care with the patient.

The preceding merely illustrates the principles of the invention. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety.

The applicant reserves the right to physically incorporate into this specification any and all materials and information from any such patents, publications, scientific articles, web sites, electronically available information, and other referenced materials or documents to the extent such incorporated materials and information are not inconsistent with the description herein.

The written description portion of this patent includes all claims. Furthermore, all claims, including all original claims as well as all claims from any and all priority documents, are hereby incorporated by reference in their entirety into the written description portion of the specification, and Applicant(s) reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun.

Other embodiments are within the following claims. Therefore, the patent may not be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

Therefore, provided herein is a new and improved disposable stabilization clip/clamp device for use in the securing of an orogastric feeding tube (OGT) to an endotracheal tube (ETT). The disposable stabilization clip/clamp device for use in the securing of an orogastric feeding tube (OGT) to an endotracheal tube (ETT), according to various embodiments of the present invention, offers the following advantages: ease of use; lightness in weight; durability; disposability; ease of attaching the clip/clamp device to the OGT and ETT; ease of removal of the clip/clamp device from the OGT and ETT; reduced likelihood of the OGT becoming dislodged from the ETT; reduced ability of the clip/clamp to accumulate bacteria; and the ability to be able to clean underneath of the ETT. In fact, in many of the preferred embodiments, these advantages of ease of use, lightness in weight, durability, disposability, ease of attaching the clip/clamp device to the OGT and ETT, ease of removal of the clip/clamp device from the OGT and ETT, reduced likelihood of the OGT becoming dislodged from the ETT, reduced ability of the clip/clamp to accumulate bacteria, and the ability to be able to clean underneath of the ETT are optimized to an extent that is considerably higher than heretofore achieved in prior, known clip/clamp devices for use in the securing of an orogastric feeding tube (OGT) to an endotracheal tube (ETT).

I claim:

1. A stabilization clip for use in the securing of an orogastric feeding tube to an endotracheal tube, comprising:
   a base having a first end and a second end, wherein the base includes an orogastric feeding tube holder for holding a portion of an orogastric feeding tube and an endotracheal tube holder for holding a portion of an endotracheal tube such that the endotracheal tube holder is located adjacent to the orogastric feeding tube holder;
   a hinge operatively connected to a first end of the base;
   a flexible arm having a first end and a second end such that the first end of the flexible arm is operatively connected to the hinge, wherein the flexible arm includes an elongated, flexible orogastric feeding tube tongue located adjacent to the hinge, and an elongated, flexible endotracheal tube tongue located adjacent to the orogastric feeding tube tongue such that the orogastric feeding tube tongue will protrude only over the portion of the orogastric feeding tube and the endotracheal tube tongue will protrude over the portion of the orogastric tube and the portion of the endotracheal tube, wherein the orogastric feeding tube tongue only interacts with the orogastric feeding tube and the endotracheal tube tongue only interacts with the endotracheal tube in order to secure the orogastric feeding tube to the endotracheal tube, and wherein a longitudinal recess is located between the orogastric feeding tube tongue and the endotracheal tube tongue;
   a locking mechanism located on the second end of the base; and
   an extension located on the second end of the flexible arm, wherein when the extension is located within the locking mechanism, the clip secures the orogastric feeding tube to the endotracheal tube.

2. The stabilization clip for use in the securing of an orogastric feeding tube to an endotracheal tube, according to claim 1, wherein the clip is a one-piece stabilization clip.

3. The stabilization clip for use in the securing of an orogastric feeding tube to an endotracheal tube, according to claim 1, wherein the orogastric feeding tube holder and the endotracheal tube holder are C-shaped.

4. The stabilization clip for use in the securing of an orogastric feeding tube to an endotracheal tube, according to claim 1, wherein the base is further comprised of:
  a release lever located adjacent to the locking mechanism for unlocking the locking mechanism.

5. The stabilization clip for use in the securing of an orogastric feeding tube to an endotracheal tube, according to claim 1, wherein the endotracheal tube tongue extends over the orogastric feeding tube and the endotracheal tube and the orogastric feeding tube tongue extends over the orogastric feeding tube.

6. The stabilization clip for use in the securing of an orogastric feeding tube to an endotracheal tube, according to claim 1, wherein the stabilization clip is constructed of:
  a durable, medical grade, antimicrobial, flexible, disposable material.

7. An orogastric feeding tube and endotracheal tube securing clamp, comprising:
  a base having a first end and a second end, wherein the base includes an orogastric feeding tube holder for holding a portion of an orogastric feeding tube and an endotracheal tube holder for holding a portion of an endotracheal tube such that the endotracheal tube holder is located adjacent to the orogastric feeding tube holder;
  a hinge operatively connected to a first end of the base;
  a flexible arm having a first end and a second end such that the first end of the flexible arm is operatively connected to the hinge, wherein the flexible arm includes an elongated, flexible orogastric feeding tube tongue located adjacent to the hinge, and an elongated, flexible endotracheal tube tongue located adjacent to the orogastric feeding tube tongue such that the orogastric feeding tube tongue will protrude only over the portion of the orogastric feeding tube and the endotracheal tube tongue will protrude over the portion of the orogastric tube and the portion of the endotracheal tube, wherein the orogastric feeding tube tongue only interacts with the orogastric feeding tube and the endotracheal tube tongue only interacts with the endotracheal tube in order to secure the orogastric feeding tube to the endotracheal tube, and wherein a longitudinal recess is located between the orogastric feeding tube tongue and the endotracheal tube tongue;
  a locking mechanism located on the second end of the base; and
  an extension located on the second end of the flexible arm, wherein when the extension is located within the locking mechanism, the clip secures the orogastric feeding tube to the endotracheal tube.

8. The orogastric feeding tube and endotracheal tube securing clamp, according to claim 7, wherein the clamp is a one-piece clamp.

9. The orogastric feeding tube and endotracheal tube securing clamp, according to claim 7, wherein the orogastric feeding tube holder and the endotracheal tube holder are C-shaped.

10. The orogastric feeding tube and endotracheal tube securing clamp, according to claim 7, wherein the base is further comprised of:
  a release lever located adjacent to the locking mechanism for unlocking the locking mechanism.

11. The orogastric feeding tube and endotracheal tube securing clamp, according to claim 7, wherein the clamp is constructed of:
  a durable, medical grade, antimicrobial, flexible, disposable material.

12. The orogastric feeding tube and endotracheal tube securing clamp, according to claim 7, wherein the endotracheal tube tongue extends over the orogastric feeding tube and the endotracheal tube and the orogastric feeding tube tongue extends over the orogastric feeding tube.

* * * * *